United States Patent [19]
Sibalis

[11] Patent Number: 5,336,168
[45] Date of Patent: * Aug. 9, 1994

[54] PULSATING TRANSDERMAL DRUG DELIVERY SYSTEM

[75] Inventor: Dan Sibalis, Stony Brook, N.Y.

[73] Assignee: Drug Delivery Systems Inc., New York, N.Y.

[*] Notice: The portion of the term of this patent subsequent to May 17, 2011 has been disclaimed.

[21] Appl. No.: 864,645

[22] Filed: Apr. 7, 1992

Related U.S. Application Data

[63] Continuation of Ser. No. 598,803, Oct. 4, 1990, and a continuation of Ser. No. 323,109, Mar. 13, 1989, abandoned, and a continuation of Ser. No. 55,518, May 28, 1987, abandoned.

[51] Int. Cl.$^5$ ............................................. A61N 1/30
[52] U.S. Cl. .................................. 604/20; 604/49; 128/898
[58] Field of Search ............... 128/798, 802, 803, 898; 604/20, 49; 607/149–153

[56] References Cited

U.S. PATENT DOCUMENTS

| | | | |
|---|---|---|---|
| 4,141,359 | 2/1979 | Sacabsen et al. | 604/20 |
| 4,301,794 | 11/1981 | Tapper | 604/20 |
| 4,340,047 | 7/1982 | Tapper et al. | 604/20 |
| 4,406,658 | 9/1983 | Lattin et al. | 604/20 |
| 4,764,164 | 8/1988 | Sasaki | 604/20 |
| 4,786,277 | 11/1988 | Powers et al. | 604/20 |
| 4,786,278 | 11/1988 | Masaki | 604/20 |

*Primary Examiner*—C. Fred Rosenbaum
*Assistant Examiner*—Michael Rafa
*Attorney, Agent, or Firm*—Lackenbach Siegel Marzullo Aronson & Greenspan

[57] ABSTRACT

An electrophoretic/electro-osmotic transdermal drug delivery system for passing at least one drug, or therapeutic compound, through the skin membrane of a patient by way of a drug reservoir or gel for delivery to the systemic blood of a patient in selected, periodic pulsations. The system can be varied to accommodate various types of therapeutic compounds having varied characteristics and purposes. The system includes a current oscillator that applies periodic electrical variations to the system in order to trigger rhythmical variations of the potential and resistance of the skin membrane so as to cause oscillatory electro-osmotic streaming of the liquid with the therapeutic compound across the skin membrane in synchronization with the oscillator to the systemic blood of the patient in response to the rhythmical variations. The oscillator causes the power source to deliver a periodic pulsating current that alternates with periods of no current in the system or that alternates with periods of a different current. The pulsating current is of greater value than the; different current. The pulsating current is applied for relatively short periods relative the periods of non-current or the periods of different current. The different current can be either positive or negative current. During periods of negative current the liquid with the therapeutic compound can tend to be drawn from the skin membrane into the drug reservoir or gel.

17 Claims, 3 Drawing Sheets

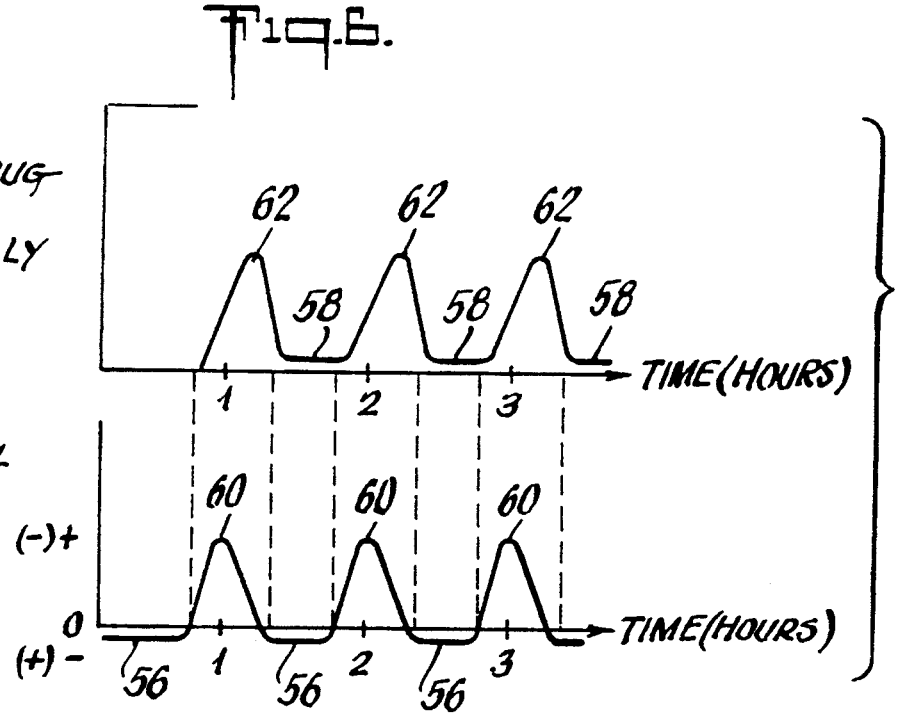
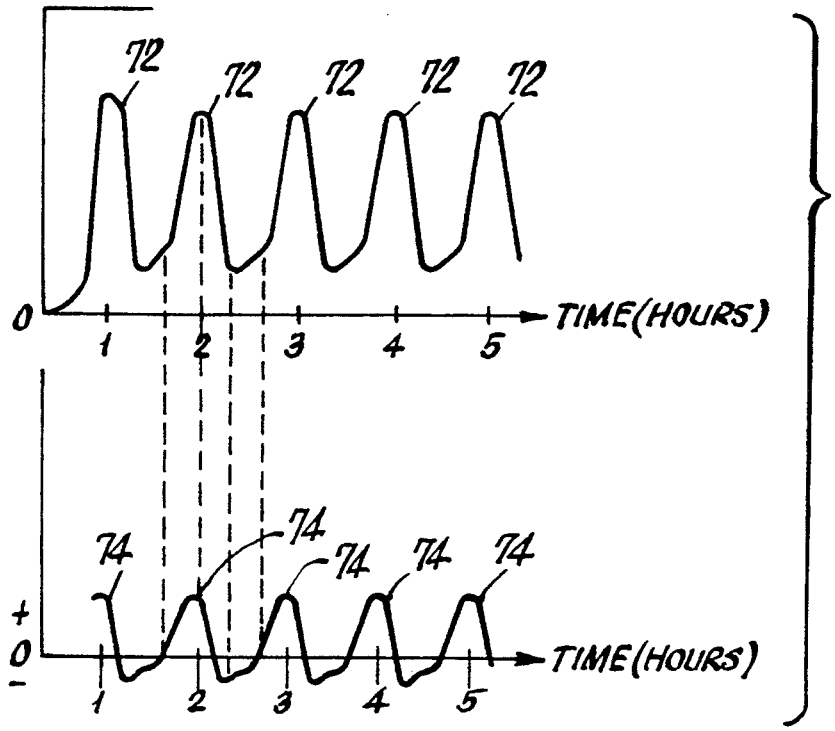

PULSATING TRANSDERMAL DRUG DELIVERY SYSTEM

RELATED U.S. PATENT APPLICATIONS

This is a continuation of application Ser. No. 598,803, filed Oct. 4, 1990, and a continuation of Ser. No. 323,109, filed Mar. 13, 1989, now abandoned, and a continuation of Ser. No. 055,518, filed May 28, 1987, now abandoned.

FIELD OF THE INVENTION

The present invention relates to transdermal drug delivery, or drug applicator, systems and more particularly to electrophoretic transdermal drug delivery systems including electro-osmotic and iontophoretic systems that function by passing an electrical current through a drug patch.

BACKGROUND OF THE INVENTION

Delivery of drugs to the systemic blood of a patient by means of an electrophoretic/electro-osmotic transdermal system is generally accomplished primarily through the sweat and sebaceous ducts and their respective glands. Some delivery is made through the stratum cornum, or horny layer. The stratum cornum, although very thin, is resistant to the passage of both electrical current and of liquids. The skin ducts cover an area of about one-thousandth of the stratum cornum.

The drug delivery system of my patent application entitled "Transdermal Drug Delivery System" Ser. No. 028679, filed Mar. 20, 1987, describes a semi-dry drug patch and a selected current level delivered to the semi-dry patch that combine to limit liquid containing a drug from moving from the patch to the skin through the sweat and sebaceous ducts so as to starve the skin ducts of liquid and divert the current and the electro-osmotic delivery of the drug through the stratum cornum. A replenishment of the skin ducts with liquid occurs at periodic intervals by an electro-osmotic delivery of the drug solution through the skin ducts. An electrical oscillator can be added to the system so as to apply periodic current increases or pulsations in order to evacuate the skin ducts of water at intervals thus removing these electrical shunts from the delivery system.

The skin of a human is of the type having skin ducts, type which is common to certain animals such as a horse, and so differs from the skins of animals not having skin ducts, such as a rabbit. Nevertheless, the human skin also has characteristics taken in toto, not only separate duct and stratum cornum characteristics, and therefore can be considered as a unitary cell membrane.

An article that discusses electro-osmotic processes of living membranes is "Electrokinetic Membrane Processes in Relation to Properties of Excitable Tissues" by Torsten Teorell, published in *Journal of General Physiology*, 1959, Vol. 42, No. 4. A constant electrical current of a first value was applied to a porous, charged membrane corresponding to an excitable cell membrane. The result was a repetitive oscillatory process wherein the membrane at first periodically increased and decreased in resistance over approximate half-hour time periods in what the author described as oscillations. The decreased level of cell membrane resistance corresponded to oscillatory streaming of water solution across the cell membrane. The repetitive oscillations dampened after about an hour and about three oscillations. When a constant electrical current of a second value slightly greater than the first current value was applied to the same membrane, the repetitive oscillations became undamped, that is, the oscillations continued at about half-hour (in fact, slightly less) periods as long as the higher current continued to be applied. The "constant" electrical current in fact naturally increased and decreased in response to lower and higher resistance states of the membrane.

Two different types of drugs, or therapeutic compounds, can be delivered to the body. The therapeutic compound can be either a first type that corresponds to a naturally released body compound, such as a hormone as insulin, or a second type that is foreign to the body, such as nitroglycerin, a cardiovascular drug, an oncological drug, and an analgesic drug.

It is a phenomenon of many therapeutic compounds of the first type that when they are delivered to the systemic blood of the patient in an oscillatory, or pulsating mode, two different effects will occur depending upon the frequency of the drug delivery time relative to the natural delivery rhythm of the body. If a therapeutic compound of the first type is delivered in periodic variations which are applied in similar rhythms as the natural delivery rhythms of the body, the activity of the naturally released body compound will be simulated. If such a therapeutic compound is delivered in periodic electrical variations which are applied more often than the natural delivery rhythms of the body, the natural activity of the body compound will be inhibited or extinguished.

It is also a phenomenon of many therapeutic compounds of the second type that when they are delivered to the systemic blood of the patient in an oscillatory mode as compared to a steady state mode of delivery, a different effect on the patient occurs as compared to the steady state mode. The oscillatory mode is selected in accordance with body requirements.

An example of a therapeutic compound of the first type that corresponds to a natural compound of the body is luteinising hormone-releasing hormone, or LHRH, which is also known as a gonadotrophin releasing hormone, or GnRH, and which controls production of testosterone in males and inducement of ovulation in females. LHRH is released in accordance with the natural rhythm of the body for approximately 6 minutes every hour. A transdermal drug delivery system that delivers LHRH in a steady state mode or at an increased frequency from the natural frequency extinguishes gonadotrophic secretion: That is, the production of either testosterone in males or ovulation females ceases. On the other hand, a transdermal delivery system that delivers LHRH in a correct pulsating mode in accordance with the natural rhythm of the body simulates, or ensures, the mentioned processes. A natural compound of the body such as LHRH is released in accordance with a natural release rhythm of the body. In the case of LHRH and many other natural compounds there exist active analogues that have certain advantages over the particular natural compound. These active analogues are often used rather than the natural compounds to trigger or to inhibit or extinguish body responses.

An example of a drug of the second type that is foreign to the body is nitroglycerin. It is known that the steady state delivery of nitroglycerin to a heart patient via a transdermal drug delivery system results in a build-up of a tolerance to the drug by the body of the patient in less than 24 hours so that the drug is rendered useless for the 24-hour prophylaxis of stable angina pectoris. This matter is discussed in a paper entitled "Transdermal Nitroglycerin Patches in Angina Pectoris" by Udho Thadani et al., published in "Annals of Internal Medicine" October 1986, Vol. 105, No. 4.

It is known that a pulsating electrical current can be applied to an electrical circuit by various means, for example, by an oscillator in the circuit. Pulsations of potential or current in a an electrophoretic drug delivery system that are timed in accordance with an interplay of driving forces present in the drug delivery system including the skin as a transmembrane can accomplish timed drug deliveries that are more precise, reliable, and efficient than with delivery being made by the natural undamped rhythmical variations of the transmembrane potential and resistance caused by a selected steady state electrical current applied to the system. The term pulsation as used herein is a periodic increase or decrease of a quantity, with the quantity herein having reference to the quantity of either potential or current or amount of a liquid with a drug transported across the transdermal skin membrane.

In general, the present invention is applicable to drug delivery systems which involve drugs or therapeutic compounds whose delivery is dependent upon timing, quantity, and direction of current flow.

It is an object of this invention to provide an electrophoretic/electro-osmotic transdermal drug delivery system that rhythmically delivers a therapeutic compound, or drug, to the systemic blood of a patient in response to application of current pulsations to the system which is otherwise devoid of current.

It is-another object of this invention to provide an electrophoretic/electro-osmotic transdermal drug delivery system that rhythmically delivers a therapeutic compound to the systemic blood of a patient by application of positive current pulsations with a negative current being alternately applied to the system.

It is another object of this invention to provide an electrophoretic/electro-osmotic transdermal drug delivery system that rhythmically delivers a therapeutic compound to the systemic blood of a patient by application of negative current pulsations with a positive current being alternately applied to the system.

It is another object of this invention to provide an electrophoretic/electro-osmotic transdermal drug delivery system that rhythmically delivers a therapeutic compound to the systemic blood of a patient by application of positive current pulsations with a different positive current being alternately applied to the system.

It is another object of this invention to provide an electrophoretic/electro-osmotic transdermal drug delivery system that rhythmically delivers a therapeutic compound to the systemic blood of a patient by application of negative current pulsations with a different negative current being alternately applied to the system.

It is another object of this invention to provide an electrophoretic/electro-osmotic transdermal drug delivery system that rhythmically delivers a therapeutic compound to the systemic blood of a patient by application of current pulsations so as to reinforce the natural delivery rhythms of the body.

It is another object of this invention to provide an electrophoretic/electro-osmotic transdermal drug delivery system that rhythmically delivers a therapeutic compound to the systemic blood of a patient by application of current pulsations so as to inhibit or negate the natural delivery rhythms of the body.

In accordance with these and other objects there is described herein an electrophoretic/electro-osmotic transdermal drug delivery system for passing at least one therapeutic compound through the skin membrane of a patient by way of a drug patch for delivery to the systemic blood of a patient in selected, periodic pulsations. The system can be varied to accommodate various types of therapeutic compounds having varied characteristics and purposes. The system includes a current oscillator that applies periodic electrical variations to the system in order to trigger rhythmical variations of the potential and resistance of the skin membrane in synchronization with the oscillator so as to cause oscillatory electro-osmotic streaming of the liquid with the therapeutic compound across the skin membrane to the systemic blood of the patient in response to the rhythmical variations. The oscillator causes the power source to deliver a periodic pulsating current that alternates with periods of no current in the system or that alternates with periods of a different current than the pulsating current. The pulsating current can be applied for relatively short periods relative the periods of noncurrent or the periods of different current or can be applied for long periods relative the periods of noncurrent of the periods of different current. The different current can be either positive or negative current. During the periods of negative current the liquid with the therapeutic compound tends to be drawn from the skin membrane into the drug patch.

BRIEF DESCRIPTION OF THE DRAWINGS

FIG. 6 is a model graph that illustrates delivery of a therapeutic compound to the skin of a patient by alternating negative and positive pulsating current delivery;

FIG. 8 is a model graph that illustrates flow of drug solution across the skin in response to pulsating voltage application to the system.

DESCRIPTION OF THE PREFERRED EMBODIMENT

Reference is now made in detail to the drawings wherein the numerals refer to the same or similar elements throughout.

Figure 1:
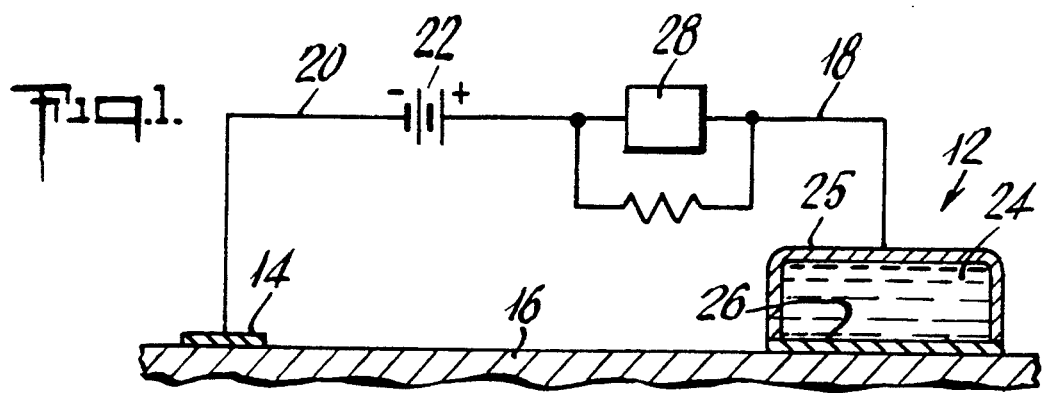
FIG. 1 is a schematic representation of an electrophoretic drug delivery system having a drug patch in osmotic contact with the skin of a patient and including an oscillator that acts as a switch for the battery in the system.

An electrical schematic diagram of an electrophoretic drug delivery system in accordance with the present invention shown in FIG. 1 includes a drug storage patch, shown for purposes of exposition as a reservoir 12, and an electrode 14 each in contact with the skin, or cell membrane, 16 of a patient. Reservoir 12 and electrode 14 are connected by conductors 18 and 20, respectively, to the positive and negative terminals, or poles, of a battery 22. Reservoir 12 includes a liquid suspension, or solution, 24 containing a therapeutic compound to be delivered to the systemic blood of the patient. Solution 24 is contained by a cover 25 and a semipermeable adhesive gel 26 integral with cover 25 and which is in contact with skin 16. The therapeutic compound to be delivered to the patient is shown by way of example to be stored in the membrane-sealed drug reservoir described, but the therapeutic compound could be stored in a gel, or matrix, holding the therapeutic compound in a liquid suspension, or solution, throughout. A timer, or oscillator, 28 is connected to the circuit. The timer or oscillator 28 causes current received from battery 22 to be applied as current pulsations to reservoir 12 at selected periodic, or rhythmical, intervals so that the liquid in solution 24 along with the therapeutic compound is transported from reservoir 12, which is in osmotic contact with skin 16, through skin 16 to the systemic blood of the patient in undamped oscillatory processes in response to the rhythmical applications of the current.

Oscillator 28 causes periodic electrical pulsations to be applied to the circuit and particularly to reservoir 12 so as to trigger rhythmical variations of the potential and resistance of skin membrane 16 in synchronization with oscillator 28 so as to cause oscillatory electroosmotic streaming of the liquid with the drug from reservoir 12 across skin membrane 16 to the systemic blood of the patient in response to the mentioned rhythmical variations of skin membrane 16.

Figure 2:
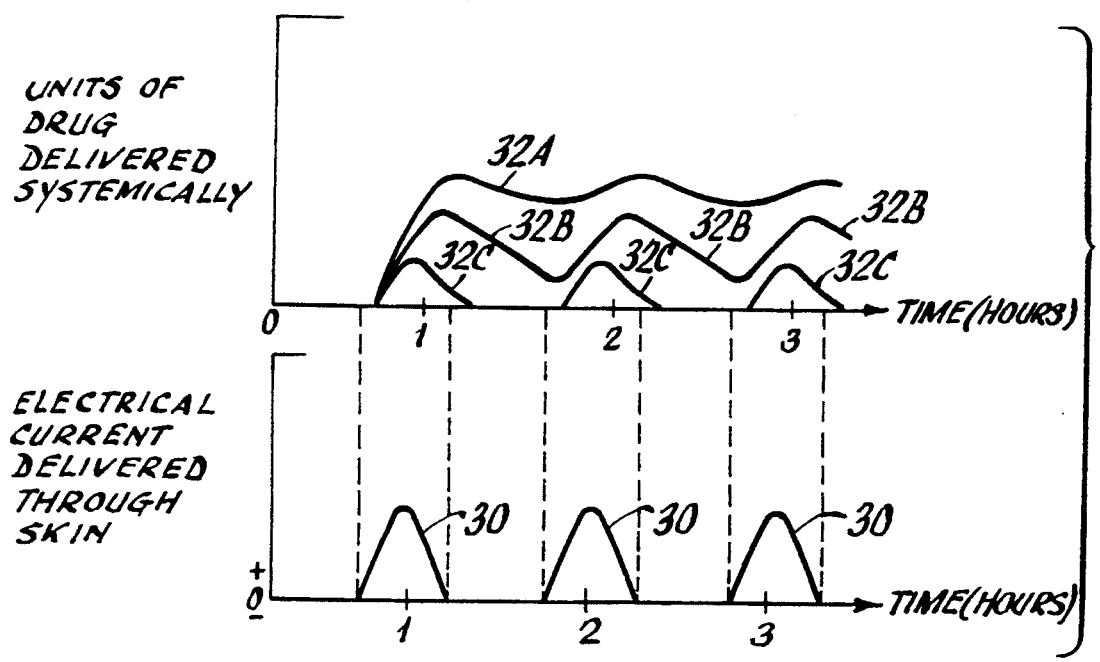
FIG. 2 is a model graph that illustrates delivery of a therapeutic compound to the skin of a patient by application of a pulsating current to a system otherwise devoid of current in accordance with the system shown in FIG. 1.

FIG. 2 shows a model graph that illustrates a particular drug delivery system in accordance with the present invention and the schematic diagram illustrated in FIG. 1. Current pulsations 30 are delivered to reservoir 12, and pulsating amounts of drug 32 are transported across skin 16 by oscillatory streaming to the systemic blood of the patient in response to the rhythmical variations of pulsations 30. Current pulsations 30 are shown as being delivered at periodic one hour intervals for purposes of exposition, but the intervals could be between a few minutes to a number of hours. Oscillatory amounts of drug delivered increase gradually in response to pulsations 30, then over the next hour gradually decrease in accordance with the depletion of the drug in skin 16. A small amount of the drug is still retained in skin 16 when the next current pulsation 30 is triggered by oscillator 28 and skin 16 again responds in an oscillatory process by transporting the drug to the systemic blood of the patient. In this manner a predictable supply of the drug is delivered to the patient in a predetermined manner. Delivery of drugs A, B, and C having long, medium, and short half-lives 32A, 32B, and 32C, respectively, are illustrated. The time in the ordinate axis is also a function of the transit time for the particular drug. A long half-life drug A is delivered at a substantially steady state delivery mode that is highly advantageous over a delivery by a steady state current in that the total amount of current delivered is reduced with the result that electrochemical changes by the current of drug A in the drug reservoir is reduced. A medium half-life drug B is illustrated with a substantial pulsating delivery to the systemic blood. A short half-life drug C, such as LHRH, has defined pulsations 32C. If, for example, electrical pulsations 30 were applied so as to cause drug pulsations 32C to last for 6 minutes every hour, this drug system would ensure a natural supply of LHRH over an extended period of time with the result that the production of testosterone in males or or induction of ovulation in females would be produced. If the system were designed to deliver electrical pulsations 30, for example, two or more times an hour, the gonadotrophic secretion would be extinguished in both males and females. Such a system is useful in birth control and in treatment of cancers. The start and finish of each drug delivery pulsation slightly lags the start and finish of each electrical pulsation.

Figure 3:
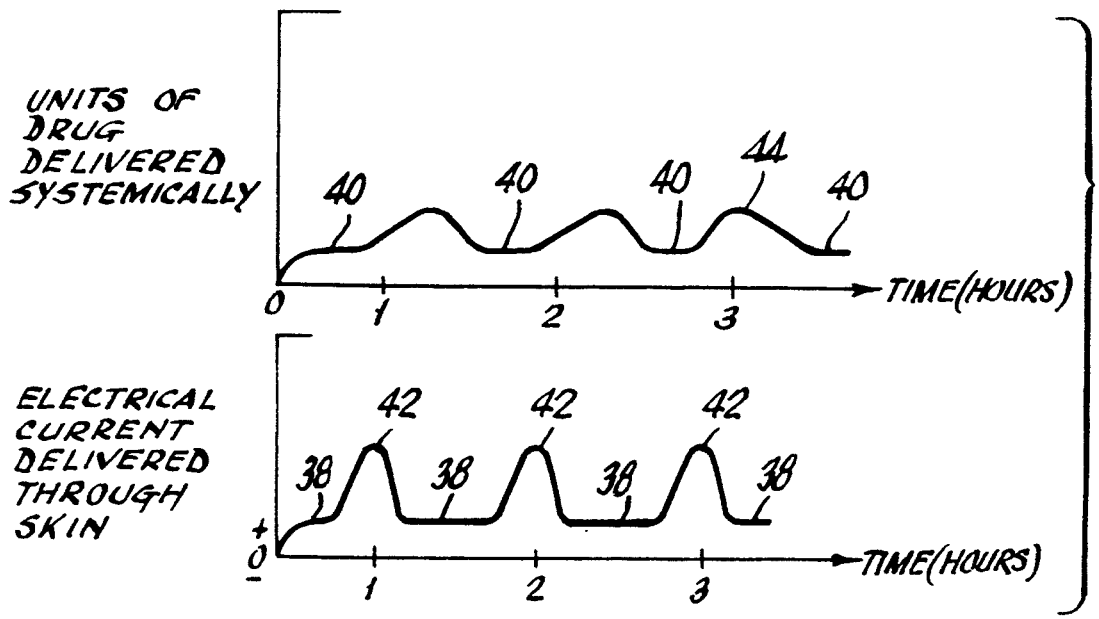
FIG. 3 is a model graph that illustrates delivery of a therapeutic compound to the skin of a patient by both a positive current delivery and positive pulsating current delivery in accordance with the system shown in FIG. 1.

In another embodiment of the invention, an electrophoretic drug delivery system in accordance with the schematic diagram shown in schematic in FIG. 1 is illustrated in a model graph in FIG. 3. Battery 22 ordinarily delivers a positive current 38 and in response an amount of drug 40 is delivered to the systemic blood of the patient. Oscillator 36 causes current value increases, or pulsations, 42, which are greater than current 38, to be delivered to skin 16, which in response transports the liquid with the drug in undamped oscillatory streaming across skin 16 to the systemic blood of the patient shown as oscillatory amounts of drug delivered 44. Current pulsations 42 are shown as being delivered at periodic one hour intervals for purposes of exposition, but the periodic intervals could be spaced between a few minutes to a number of hours. Amounts of drug delivered 44 increase gradually in response to pulsations 42, then over the next hour gradually decreases towards amount of drug delivered 40 in accordance with the depletion of liquid in skin 16. When the next current pulsation 42 is triggered by oscillator 36, skin 16 again responds in the oscillatory process by again transporting the drug to the systemic blood of the patient. In this manner alternate amounts of drug 40 and pulsating amounts of drug 44 are delivered to the systemic blood of the patient. Although only one drug is shown, variations of the drug delivered in accordance with drugs having long, medium, and short half-lives as shown in FIG. 2 can also be used in the system of FIG. 3.

The system shown in FIG. 3 is advantageous for the delivery of insulin to a patient. The body requirements of insulin are that it must be continuously delivered to a patient, but extra quantities are required at certain times such as after meals. Oscillator 36 can be set to or triggered to follow meals of the patient.

Another type of drug that can be used with the drug delivery system shown in FIG. 3 is one of the anti-cancer drugs, which are most effective in the night hours when such a drug is less toxic to the patient as it can be during daytime hours.

Figure 4:
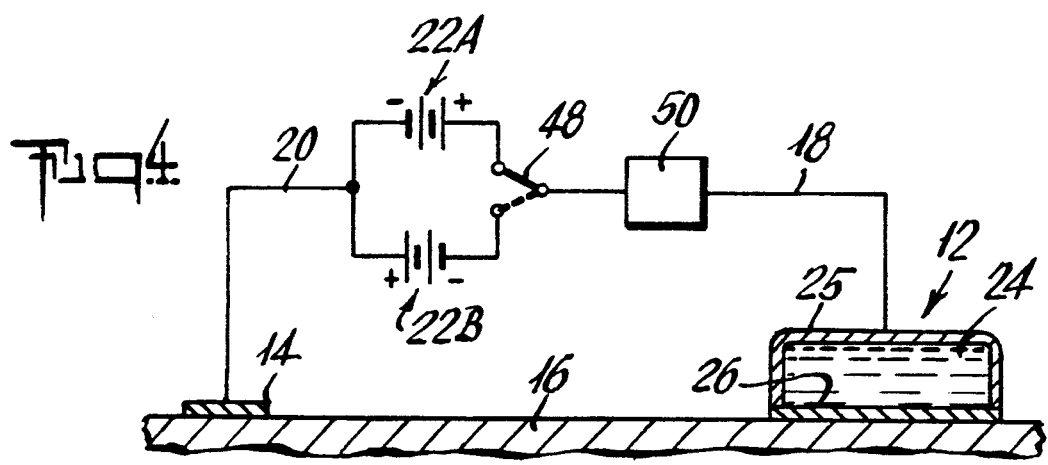
FIG. 4 is a schematic representation of an electrophoretic drug delivery system that supplies both a positive and a negative current to the drug patch and that includes two batteries of opposite polarity in parallel in the system and a switch for reversing the current flow so as to supply alternating positive and negative pulsations.

Another embodiment of the present invention is a drug delivery system shown in an electrical schematic diagram in FIG. 4. A pair of batteries 22A and 22B in parallel in the circuit are oriented in opposed polar relationship with the circuit. A switch 48 connected to both batteries 22A and 22B can be operated to alternately bring either battery 22A or 22B into the circuit with the result that the direction of current flow in the circuit is alternatively reversed. A timer, or oscillator, 50 causes switch 48 to be operated at periodic intervals. Battery 22B generates a negative current at drug reservoir 12. Negative current at drug reservoir 12 draws liquid with the drug present in skin membrane 16 into solution 24 in drug reservoir 12. This action inhibits residues of the drug in skin membrane 16 from passing into the systemic blood of the patient. At selected periodic intervals the timer activates oscillator 50 to operate switch 48 so as to bring battery 22A into the circuit and isolate battery 22B from the circuit. The positive current that is generated by battery 22A is a much greater current than the low negative current generated by battery 22B and in addition is applied for short pulsation periods rather than the long pulsation periods of the negative current. In response to the rhythmical applications of the positive current, the liquid in solution 24 along with the drug is transported from reservoir 12 into skin 16 to the systemic blood of the patient in oscillatory processes. At the end of each pulsation period, oscillator 50 operates switch 48 to deactivate battery 22A and activate battery 22B so as to create once again an alternate negative current at reservoir 12.

Figure 5:
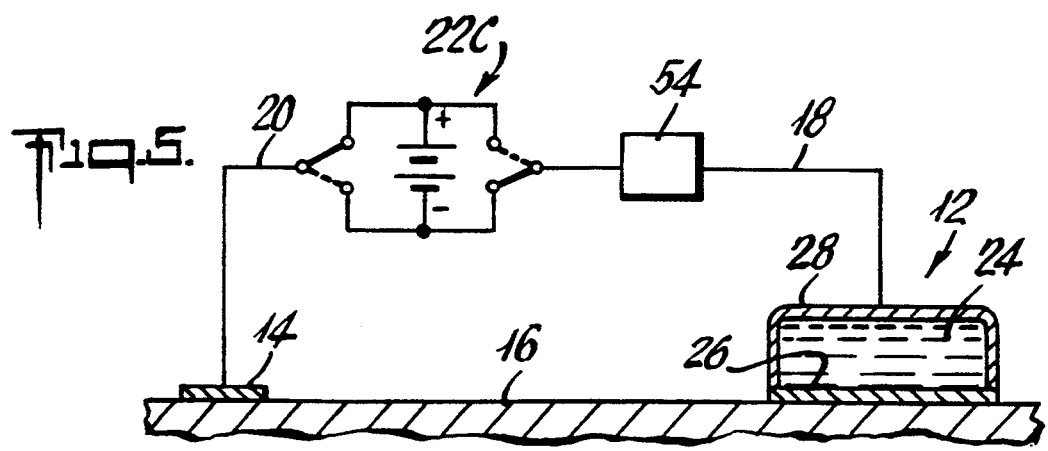
FIG. 5 is a schematic representation of an electrophoretic drug delivery system that supplies both a positive and a negative current to the drug patch and that includes a polarity-reversing double-pole, double-throw switch so as supply alternating positive and negative pulsations.

FIG. 5 illustrates an alternate schematic diagram embodiment to the system shown in FIG. 4. A single battery 22C is connected to a solid state, double-pole, double-throw switch 52 that can be activated by an oscillator 54 to reverse the direction of flow of current from positive to negative and the reverse. Oscillator 54 causes a positive current to flow to drug reservoir 12 when switch 52 is activated in one current flow direction, and causes a negative current to flow to drug reservoir 12 when switch 52 is activated in the opposite current flow direction.

FIG. 6 shows a model graph that illustrates a drug delivery system according to FIGS. 4 and 5. A negative current 56 is generated either by battery 22B or by battery 22C so that a very low amount of drug 58 at a level that is substantially zero is delivered to the systemic blood of the patient during the application of negative current 56. The reason for this phenomenon is that it is difficult to totally prevent drug migration into the body of the patient once the drug is in skin membrane 16. Positive current pulsations 60 are generated either by battery 22A or by battery 22B so as to trigger rhythmical variations of the potential and resistance of skin membrane 16 in synchronization with current pulsations 60 so as to cause oscillatory electro-osmotic streaming of the liquid with the drug across skin membrane 16 to the systemic blood of the patient in amounts of drug delivered 62 in response to the mentioned rhythmical variations. Drugs having long, medium, and short half-lives analogous to drugs A, B, and C shown in FIG. 2 can be used in the system illustrated in FIG. 6.

An inverted image of the electrical current of the graph illustrated in FIG. 6 is possible as indicated by the reversed positive and negative signs in parenthesis. The graph of FIG. 6 and the inverted image of the graph relate to drugs that migrate from different poles.

Figure 7:
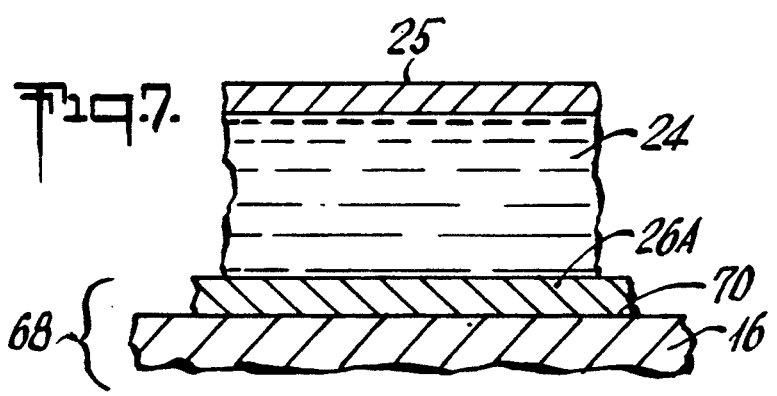
FIG. 7 illustrates in isolated cross-section an integral cell membrane that includes a semipermeable membrane joined with the cover of the drug reservoir in adhesive and osmotic contact with the skin so as to form a cell membrane integral with the skin.

FIG. 7 illustrates an integral excitable, or oscillatory, membrane 68 that includes an adhesive gel semipermeable membrane 26A connected with cover 25 surrounding drug solution 24. Integral oscillatory membrane 26A is in contact with skin 16 of a patient. An adhesive hydrogel interface 70 is positioned between integral oscillatory membrane 26A and skin 16. Skin 16 is a part of integral oscillatory membrane 68. When integral oscillatory membrane 68 is positioned in the schematic systems illustrated in FIGS. 1, 4, and 5, analogous results to the drug delivery systems shown in the model graphs of FIGS. 2, 6, and 7 can be obtained with integral oscillatory membrane 68 acting as a unified oscillatory membrane rather than skin 16 alone.

FIG. 8 is a model graph illustrating a pulsating voltage 72 applied to the systems described in FIG. 1. A net flow, or flux, of the drug solution is shown in movement across skin 16 or integral membrane 68. A positive flux 74 results when voltage 72 is increased and a negative flus 76 results when voltage 72 is decreased. The reason for this phenomenon is the coupling between three driving forces of the pulsating system, namely, gradients of drug concentration, membrane potential, and hydrostatic pressure within a charged membrane and in addition the presence of a time delay of the resistance change of the membrane.

Although the present invention has been described in some detail by way of illustration and example for purposes of clarity and understanding, it will, of course, be understood that various changes and modifications made in the form, details, and arrangements of the parts without departing from the scope of the invention as set forth in the following claims.

What is claimed is:

1. An electrolytic transdermal patch for delivering to the bloodstream of a patient different types of drugs comprising:
   (a) means defining a reservoir for containing a drug of said types of drugs and positioned in use in contact with the skin of the patient,
   (b) an electrical source of power,
   (c) an electrical circuit having an electrode positioned in use in contact with the skin of the patient and electrically connecting the electrode, power source and said reservoir; and
   (d) means in said electrical circuit for causing periodic variation of current applied to said reservoir by said source of power in a pulsed mode in synchronization with a natural rhythmical variations of response to a drug by the patient when said drug is foreign to the body of the patient.

2. The system of claim 1, wherein said means for effecting pulsation alternately applies a positive first current and a positive second current to said electrical circuit, said positive second current being greater in value than said positive first current.

3. The system of claim 1 wherein said means for effecting pulsation alternately applies a positive first current and a positive second current to said electrical circuit, said positive second current being such greater in value than said positive first current.

4. The system of claim 1 wherein said power source includes two batteries connected to said circuit; and said means for effecting pulsation includes a switch connected with said circuit capable either of connecting one battery of said two batteries with said circuit in one polar orientation and simultaneously disconnecting the other battery of said two batteries from said circuit in the other polar direction and simultaneously disconnecting said one battery from said circuit.

5. The system of claim 4, wherein said means for effecting pulsation further includes an oscillator that alternately applies an alternating negative first current and a positive second current to said circuit.

6. The system of claim 4, wherein said means for effecting pulsation further includes an oscillator that alternately applies a positive first current and a negative second current to said circuit.

7. The system of claim 1, wherein said power source includes a battery connected to said circuit, and a solid state double-poled, double-throw switch connected to said battery, said double-throw switch being capable of reversing the polarity of said battery relative said circuit so as to reverse the direction of flow of current in said circuit.

8. The system of claim 7 wherein said means for effecting pulsation further includes an oscillator that alternately applies an negative first current and a positive second current to said circuit.

9. The system of claim 7 wherein said means for effecting pulsation further includes an oscillator that alternately applies a positive first current and a negative second current to said circuit.

10. The system of claim 1 wherein said drug is a natural compound of the body or an active analogue thereof.

11. The system of claim 1 wherein said drug is foreign to the body and said periodic variation of current are applied in accordance with the body requirements of the particular drug.

12. An electrolytic transdermal patch for delivering to the bloodstream of a patient different types of drug according to claim 1, in which said means in said electrical circuit comprises means for effecting positive current pulsations with a different positive current being alternately applied to said reservoir.

13. An electrolytic transdermal patch for delivering to the bloodstream of a patient different types of drugs according to claim 1, in which said means in said electrical circuit comprises means for effecting negative current pulsations with a different negative current alternatively applied to said reservoir.

14. An electrolytic transdermal patch for delivering to the bloodstream of a patient different types of drugs according to claim 1, in which said means in said electrical circuit comprises an oscillator.

15. An electrolytic transdermal patch for delivering to the bloodstream of a patient different types of drugs according to claim 14, in which said oscillator causes the power source to deliver a periodic pulsating current that alternates with periods of no current in the system.

16. An electrolytic transdermal patch for delivering to the bloodstream of a patient different types of drugs according to claim 1, in which said means in said electrical circuit comprises a current oscillator for effecting periodic electrical variations rhythmically to trigger rhythmical variations of the resistance of the skin in synchronization with said current oscillator to cause oscillatory electro-osmotic streaming of a liquid therapeutic drug across the skin.

17. An electrolytic transdermal patch for delivering to the bloodstream of a patient different types of drug according to claim 1, in which said in said electrical circuit means comprises an oscillator for delivering said drugs in which the delivery is dependent upon timing, quantity or direction of current flow.

* * * * *